US009675624B2

(12) United States Patent
Ignar et al.

(10) Patent No.: US 9,675,624 B2
(45) Date of Patent: Jun. 13, 2017

(54) COMBINATION OF LEVOCABASTINE AND FLUTICASONE FUROATE FOR THE TREATMENT OF INFLAMMATORY AND/OR ALLERGIC CONDITIONS

(71) Applicant: Glaxo Group Limited, Brentford, Middlesex (GB)

(72) Inventors: Diane Michele Ignar, Research Triangle Park, NC (US); Daren Scott Levin, Research Triangle Park, NC (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/652,037

(22) PCT Filed: Dec. 13, 2013

(86) PCT No.: PCT/EP2013/076486
§ 371 (c)(1),
(2) Date: Jun. 12, 2015

(87) PCT Pub. No.: WO2014/095602
PCT Pub. Date: Jun. 26, 2014

(65) Prior Publication Data
US 2015/0297614 A1    Oct. 22, 2015

Related U.S. Application Data

(60) Provisional application No. 61/867,794, filed on Aug. 20, 2013, provisional application No. 61/737,927, filed on Dec. 17, 2012.

(51) Int. Cl.
| | | |
|---|---|---|
| *A61K 31/58* | (2006.01) | |
| *A61K 31/4418* | (2006.01) | |
| *A61K 31/451* | (2006.01) | |
| *A61K 9/00* | (2006.01) | |
| *A61K 9/10* | (2006.01) | |
| *A61K 47/38* | (2006.01) | |
| *A61K 47/26* | (2006.01) | |

(52) U.S. Cl.
CPC ............ *A61K 31/58* (2013.01); *A61K 9/0043* (2013.01); *A61K 9/10* (2013.01); *A61K 31/4418* (2013.01); *A61K 31/451* (2013.01); *A61K 47/26* (2013.01); *A61K 47/38* (2013.01)

(58) Field of Classification Search
None
See application file for complete search history.

(56) References Cited

U.S. PATENT DOCUMENTS

| 3,813,384 A | 5/1974 | Brock et al. |
|---|---|---|
| 2002/0165211 A1 | 11/2002 | Biggadike et al. |

FOREIGN PATENT DOCUMENTS

| CN | 101757625 A | 6/2010 |
|---|---|---|
| WO | 2008012338 A2 | 1/2008 |

OTHER PUBLICATIONS

Han et al.; "A Multicenter Randomized Double-Blind 2-Week Comparison Study of Azelastine Nasal Spray 0.1% Versus Levocabastine Nasal Spray 0.05% in Patients with Moderate-to-Severe Allergic Rhinitis"; Journal for Oto-Rhino-Laryngology and Its Related Specialties; 2011; vol. 73, No. 5; pp. 260-265.
US FDA Approved Label for VERAMYST™ (fluticasone furoate) Nasal Spray, NDA No. 022050, Approved Apr. 27, 2007.
Corren, et al., "Onset and duration of action of levocabastine nasal spray in atopic patients under nasal challenge conditions." J. Allergy Clin. Immunol.; Apr. 1999; pp. 574-580; vol. 103, No. 4.
Murdoch, et al., "Once-daily dosing of levocabastine has comparable efficacy to twice-daily dosing in the treatment of allergic rhinitis assessed using an allergen challenge chamber." International Journal of Clinical Pharmacology and Therapeutics; 2015; pp. 811-818; vol. 53, No. 10.
Murdoch, et al., "The improved efficacy of a fixed-dose combination of fluticasone furoate and levocabastine relative to the individual components in the treatment of allergic rhinitis." Clinical & Experimental Allergy; 2015; pp. 1346-1355; vol. 45.

*Primary Examiner* — Samantha Shterengarts
(74) *Attorney, Agent, or Firm* — James P. Riek; R. Steve Thomas

(57) ABSTRACT

The present invention relates to pharmaceutical formulations comprising an anti-inflammatory glucocorticoid compound of the androstane series and levocabastine, an $H_1$ antagonist/anti-allergic, and also relates to therapeutic uses thereof, particularly for the treatment of inflammatory and allergic conditions, specifically rhinitis.

20 Claims, 14 Drawing Sheets

COMBINATION OF LEVOCABASTINE AND FLUTICASONE FUROATE FOR THE TREATMENT OF INFLAMMATORY AND/OR ALLERGIC CONDITIONS

CROSS-REFERENCE TO RELATED APPLICATIONS

This application is filed pursuant to 35 U.S.C. §371 as a United States National Phase Application of International Patent Application No. PCT/EP2013/076486 filed Dec. 13, 2013, which claims priority from Provisional Application No. 61/867,794 filed on Aug. 20, 2013 and from Provisional Application No. 61/737,927 filed on Dec. 17, 2012.

BACKGROUND OF THE INVENTION

The present invention relates to pharmaceutical formulations comprising an anti-inflammatory glucocorticoid compound of the androstane series and levocabastine, an $H_1$ antagonist/anti-allergic. The present invention also relates to therapeutic uses thereof, particularly for the treatment of inflammatory and allergic conditions, specifically rhinitis.

Many millions of individuals suffer from seasonal and perennial allergic rhinitis worldwide. Symptoms of seasonal and perennial allergic rhinitis include nasal itch, congestion, runny nose, sneezing and watery eyes. Seasonal allergic rhinitis is commonly known as 'hay fever'. It is caused by allergens which are present in the air at specific times of the year, for example tree pollen during Spring and Summer. Perennial allergic rhinitis is caused by allergens which are present in the environment during the entire year, for example dust mites, mould, mildew and pet dander.

The majority of allergic rhinitis sufferers report nasal symptoms (congestion, sneezing, itching and rhinorrhea) and ocular symptoms (redness, watery eyes, itching and burning) which impact quality of life and can also be associated with substantial healthcare costs (e.g. exacerbations of sinusitis and asthma, nasal polyps, hearing impairment, etc) and other economic impacts (e.g. less work productivity) if not treated properly.

The goal of allergic rhinitis therapy is to manage both the acute and chronic manifestations of the disease by minimising the associated symptoms and improving quality of life. To achieve this, current treatment recommendations include allergen avoidance, immunotherapy and/or pharmacotherapy. Avoidance is difficult to achieve for the most common allergens (e.g., pollen, dust mites). Immunotherapy is an effective chronic therapy in some patients but it is time-consuming, inconvenient, and has potential serious adverse effects (such as large local reactions and anaphylaxis). Current pharmacotherapy options include intranasal corticosteroids, oral and intranasal antihistamines (AH), non-steroidal anti-inflammatory agents and decongestants.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the greater the efficacy, and therefore the medicament must be capable of resisting those forces in the nasal passages that function to remove particles from the nose. Such forces, referred to as 'mucociliary clearance', are recognised as being extremely effective in removing particles from the nose in a rapid manner, for example, within 10 to 30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors. In the case of administration of glucocorticoids, the potential for any undesirable side effects should preferably be minimised.

Glucocorticoids which have anti-inflammatory properties are known and are widely used for the treatment of inflammatory disorders or diseases such as asthma and rhinitis.

Inhaled corticosteroids include beclomethasone esters (e.g. the 17-propionate ester or the 17,21-dipropionate ester), fluticasone propionate, budesonide, flunisolide, mometasone esters (e.g. the furoate ester), triamcinolone acetonide, rofleponide, and ciclesonide. Inhaled glucocorticoids are also disclosed in WO02/12265, WO02/12266, WO05/005452, WO05/005451 and WO02/088167.

WO02/12265 discloses 6α,9α-difluoro-17α-[(2-furanylcarbony)oxy]-11β-hydroxy-16α-methyl-3-oxo-androsta-1,4-diene-17β-carbothioic acid S-fluoromethyl ester, known by the generic name fluticasone fluroate.

$H_1$ antagonists/antiallergics (also referred to as antihistamines) are known and can be used in nasal sprays and eye drops to treat allergy-related conditions, such as seasonal allergic rhinitis and in the treatment of itching of the eye associated with allergic conjunctivitis. Antihistamines may be referred to as first, second or third generation antihistamines.

First generation $H_1$ antihistamines include piperoxam, ethylenediamines (e.g. mepyramine (pyrilamine), antazoline), ethanolamines (e.g. diphenhydramine, carbinoxamine, doxylamine, clemastine, and dimenhydrinate), alkylamines (e.g. pheniramine, chlorenamine (chlorpheniramine), dexchlorphenamine, brompheniramine, and triprolidine), piperazines (e.g. cyclizine, hydroxyzine, and meclizine), and tricyclics (e.g. promethazine, alimemazine (trimeprazine), cyproheptadine, and azatadine).

Second-generation antihistamines include systemic drugs (e.g. acrivastine, astemizole, cetirizine, loratadine, mizolastine, and terfenadine) and topical drugs (e.g. azelastine, levocabastine, and olopatidine). It is known that levocabastine, usually as the hydrochloride salt, for example as disclosed in U.S. Pat. No. 3,813,384, can be administered as a nasal spray to treat conditions such as rhinitis. Commercially available formulations of levocabastine are typically intended for twice daily administration.

Third generation antihistamines include levocetirizine, desloratidin and fexofenadine.

We have now identified novel formulations comprising a corticosteroid and an $H_1$ receptor antagonist. Said formulations are suitable for intranasal administration and may have advantages over those formulations already known.

BRIEF SUMMARY OF THE INVENTION

According to one aspect of the invention, there is provided a pharmaceutical formulation comprising levocabastine or a salt thereof and fluticasone furoate (FF). Levocabastine has the chemical formula (I)

and the chemical name (3S,4R)-1-[4-cyano-4-(4-fluorophenyl)cyclohexyl]-3-methyl-4-phenylpiperidine-4-carboxylic acid.

Fluticasone furoate has the chemical formula (II)

and the chemical name 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

A formulation according to the present invention may demonstrate excellent anti-inflammatory, anti-allergic and tolerability properties. The formulation may also demonstrate more rapid onset of action and improved efficacy compared to intranasal corticosteroid monotherapy and may be amenable to once-per day dosing. In addition the combination may allow lower daily dose of one or both of the components to be used leading to better tolerability/adverse event profile. The formulation may reduce or eliminate the negative taste profile associated with other intransal antihistamines.

Levocabastine may form salts with acids, for example, an inorganic acid, such as hydrohalic acide, e.g. hydrochloric or hydrobromic acid and sulphuric acid, nitric acid or phosphoric acid; or an organic acid, such as for example, acetic propanoic, 2-hydroxyacetic, 2-hydroxypropanoic, 2-oxopropanoic, propanedioic, butanedioic, (Z)-2-butenedioic, (E)-2-butenedioic, 2-hydroxybutane-dioic, 2,3-dihydrontbutanedioic, 2-hydroxy-1,2,3propanetricarbontlic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, or 4-amino-2-hydroxybenzoic acid.

In one embodiment levocabastine is employed as the hydrochloride.

In one aspect of the invention there is provided a pharmaceutical formulation wherein both fluticasone furoate and levocabastine or a salt thereof (e.g. the hydrochloride) are present in the form of suspended particles. In one aspect of the invention there is provided a pharmaceutical formulation which is an aqueous pharmaceutical formulation.

In one aspect of the invention there is provided a pharmaceutical formulation suitable for intranasal delivery.

In some embodiments the formulation will contain one or more suspending agents.

In some embodiments the formulation will contain one or more preservatives.

In some embodiments the formulation will contain one or more wetting agents.

In some embodiments the formulation will contain one or more isotonicity adjusting agents.

In some embodiments the formulation will contain a buffer.

In some embodiments the formulation will contain one or more taste-masking agents.

It will be appreciated that the formulations of the invention may contain one or more different types of excipients.

According to one aspect of the present invention there is provided a pharmaceutical formulation which comprises:
(i) an aqueous suspension of levocabastine or a salt thereof;
(ii) an aqueous suspension of fluticasone furoate;
(iii) one or more suspending agents;
(iv) one or more preservatives;
(v) one or more wetting agents;
(vi) a buffer;
(vii) one or more isotonicity adjusting agents; and optionally
(viii) one or more taste-masking agents.

In another aspect of the invention there is provided a pharmaceutical formulation which is free of preservative.

The formulations of the present invention may be stabilised by appropriate selection of pH. Typically, the pH will be adjusted to 3.0 to 8.0, in one embodiment 6.0 to 8.0, for example around 7.

Examples of pharmaceutically acceptable materials which can be used to adjust the pH of the formulation, if required, include hydrochloric acid and/or sodium hydroxide. It is also possible to add to the formulations buffer substances such as citric acid/sodium hydrogensulphate borate buffer, citric acid/citrate buffer, phosphates, such as disodium phosphate or monosodium phosphate sodium hydrogenorthophosphate, or disodium hydrogenphosphate, trometamol or equivalent conventional buffers in order to adjust the pH value of the formulation. In one embodiment the buffer comprises a phosphate buffer, for example disodium phosphate or monosodium phosphate.

The aqueous component is desirably a high grade quality of water, for example purified water.

The fluticasone furoate and levocabastine active pharmaceutical ingredients (API) will each suitably have a mass mean diameter (MMD) of less than 20 μm, in one embodiment between 0.5-10 μm, for example between 1-5 μm. If particle size reduction is necessary, this may be achieved for example by techniques such as micronisation and/or microfluidisation.

In one embodiment MMDs are between 2-4 μm.

In some embodiments, if necessary, particle size reduction may be achieved by micronisation.

In other embodiments, particle size reduction may be achieved by microfluidisation.

In one embodiment, the particles will be crystalline, prepared for example by a process which comprises mixing in a continuous flow cell in the presence of ultrasonic radiation a flowing solution of fluticasone furoate or levocabastine in a liquid solvent with a flowing liquid antisolvent for said medicament (for example, as described in WO00/38811).

In the pharmaceutical formulations of the invention, fluticasone furoate may be present within the formulation in an amount of from 0.005% to 1% (w/w), in one embodiment from 0.01% to 0.5% (w/w), for example from 0.05 to 0.1% (w/w) based on the total weight of the formulation. Typically, 50 μl of suspension will contain 27.5 μg of fluticasone furoate.

In the pharmaceutical formulations of the invention, levocabastine (the compound of formula (I)), or a salt thereof, may be present within the formulation in an amount of from 0.0005% to 2% (w/w), in one embodiment from 0.01% to 0.6% (w/w), for example from 0.1 to 0.3% (w/w) based on the total weight of the formulation. Typically, 50 μl of suspension will contain 50 $\mu$ of levocabastine.

Examples of suspending agents include cellulose, carboxymethylcellulose, veegum, tragacanth, bentonite, methylcellulose, hypromellose, and polyethylene glycols. In one embodiment the suspending agent will be microcrystalline cellulose and carboxy methylcellulose sodium, for example used as the branded product Avicel RC591 (which typically contains 87-91% microcrystalline cellulose and 9-13% carboxy methylcellulose sodium) or Avicel CL611. In one embodiment particulate microcrystalline cellulose has a particle size in the range 1 to 100 μm. We believe that Avicel RC591 acts as a suspending agent by imparting thixotropic properties to the formulation, wherein the formulation may become a stable suspension upon being stirred, shaken or otherwise disturbed.

In some embodiments, the thixotropic nature of the suspending agent will ensure that the formulation assumes a gel like appearance at rest, wherein the particulate medicament is dispersed and suspended substantially uniformly, characterised by a high viscosity value. Once the composition is subjected to shear forces, such as those caused by agitation prior to spraying, the viscosity of the formulation will decrease to such a level to enable it to flow readily through the spray device and exit as a spray of fine particles in a mist. These particles will then be capable of infiltrating the mucosal surfaces of the anterior regions of the nose (frontal nasal cavities), the frontal sinus, the maxillary sinuses and the turbinates which overlie the conchas of the nasal cavities. Once deposited, the viscosity of the formulation will increase to a sufficient level to assume its gel-like form and resist being cleared from the nasal passages by the inherent mucocillary forces that are present in the nasal cavities.

When the formulation of the present invention comprises a suspending agent, it will desirably be added in a suitable amount to achieve this function. In some embodiments the suspending agent will be present within the formulation in an amount of from 0.1 to 5% (w/w), for example 1.5% (w/w), based on the total weight of the formulation.

For stability purposes, the formulation of the present invention may be protected from microbial contamination and growth by inclusion of a preservative. Examples of pharmaceutically acceptable anti-microbial agents or preservatives that can be used in the formulation include quaternary ammonium compounds (for example benzalkonium chloride, benzethonium chloride, cetrimide, cetylpyridinium chloride and myristyl picolinium chloride), alcoholic agents (for example chlorobutanol, phenylethyl alcohol and benzyl alcohol), antibacterial esters (for example esters of para-hydroxybenzoic acid), chelating agents such as disodium edetate (EDTA), and other anti-microbial agents such as chlorhexidine (for example in the form of the acetate or gluconate), potassium sorbate, chlorocresol, sorbic acid and its salts, polymyxin, methylparaben and propylparaben.

In some embodiments the preservative may comprise disodium edetate (EDTA), which may be present within the formulation in an amount of from 0.001 to 1% (w/w), for example around 0.015% (w/w), based on the total weight of the formulation.

In some embodiments the preservative may comprise benzalkonium chloride (BKC), which may be present within the formulation in an amount of from 0.001 to 1% (w/w), for example around 0.015% (w/w), based on the total weight of the formulation.

In some embodiments, the preservative may comprise disodium edetate and benzalkonium chloride or disodium edetate and potassium sorbate, in one embodiment potassium chloride and/or disodium edetate. In another embodiment the preservative comprises disodium edetate and benzalkonium chloride.

Formulations, for example nasal formulations which contain a suspended medicament may contain a pharmaceutically acceptable wetting agent which functions to wet the particles of medicament to facilitate dispersion thereof in the aqueous phase of the composition. It is desirable that the amount of wetting agent used will not cause foaming of the dispersion during mixing.

It will be appreciated that any agent which is effective in wetting the particles and which is pharmaceutically acceptable can be used. Examples of wetting agents that can be used are fatty alcohols, esters and ethers. In one embodiment the wetting agent is a hydrophilic, non-ionic surfactant, for example polyoxyethylene (20) sorbitan monooleate (supplied as the branded product Polysorbate 80).

Wherein the formulation of the present invention comprises a wetting agent, it will desirably be added in a sufficient quantity to achieve this function. In one embodiment the wetting agent may be present within the formulation in an amount of from 0.001 to 0.05% (w/w), for example 0.025% (w/w), based on the total weight of the formulation.

The presence of an isotonicity adjusting agent is to achieve isotonicity with body fluids, for example fluids of the nasal cavity, resulting in reduced levels of irritancy associated with many nasal formulations. Examples of suitable isotonicity adjusting agents are glucose, glycerine, sorbitol, sodium chloride, dextrose and calcium chloride. In one embodiment the isotonicity adjusting agent may be dextrose, for example, anhydrous dextrose.

When the formulation of the present invention comprises an isotonicity adjusting agent it will be desirably added in a sufficient quantity to achieve this function, in one embodiment the isotonicity adjusting agent will be present within the formulation in an amount of from 0.1 to 10% (w/w), for example 5.0% w/w, based on the total weight of the formulation.

Further auxiliary substances which may, for example, be used for the formulations of the invention are: polyvinyl pyrrolidone, sorbitan fatty acid esters such as sorbitan trioleate, polyethoxylated sorbitan fatty acid ester (for example polyethoxylated sorbitan trioleate), sorbimacrogol oleate, synthetic amphotensides (tritons), ethylene oxide ethers of octylphenolformaldehyde condensation products, phosphatides such as lecithin, polyethoxylated fats, polythoxylated oleotriglycerides and polyethoxylated fatty alcohols. In this context polyethoxylated means that the relevant substances contain polyoxyethylene chains, the degree of polymerisation of which is generally between 2 to 40, in particular between 10 to 20. These substances are generally used to improve the solubility of the levocabastinecomponent.

The formulations of the present invention may also contain further excipients and/or carriers that reduce the amount of post-nasal drip, and/or minimise or mask bitter taste.

Examples of taste-masking agents include sucralose, sucrose, saccharin or a salt thereof, fructose, dextrose, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof. In one embodiment the taste-masking agent is sucralose and/or menthol.

The pharmaceutical formulation according to the invention may further comprise one or more excipients. By the term "excipient", as used herein, it is meant to mean substantially inert materials that are nontoxic and do not interact with other components of a composition in a deleterious manner including, but not limited to, pharmaceutical grades of: carbohydrates, organic and inorganic salts, polymers, amino acids, phospholipids, wetting agents, emulsifiers, surfactants, poloxamers, pluronics, and ion exchange resins, and combinations thereof, a non-exhaustive list of examples of which are provided below:

Carbohydrates, including: monosaccharides, such as, but not limited to, fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof;

Organic and inorganic salts, including but not limited to sodium or calcium phosphates, magnesium stearate, and combinations and derivatives thereof;

Polymers, including: natural biodegradable protein polymers including, but not limited to, gelatin and combinations and derivatives thereof;

Natural biodegradable polysaccharide polymers including, but not limited to, chitin and starch, crosslinked starch and combinations and derivatives thereof;

Semisynthetic biodegradable polymers including, but not limited to, derivatives of chitosan;

Synthetic biodegradable polymers including but not limited to polyethylene glycols (PEG), polylactic acid (PLA), synthetic polymers including but not limited to polyvinyl alcohol and combinations and derivatives thereof;

Amino acids including but not limited to including nonpolar amino acids, such as leucine and combinations and derivatives thereof;

Phospholipids, including lecithins and combinations and derivatives thereof;

Wetting agents/Surfactants/Emulsifiers, including, but not limited to gum acacia, cholesterol, fatty acids including, combinations and derivatives thereof;

Poloxamers/Pluronics: including but not limited to poloxamer 188, Pluronic® F-108, and combinations and derivations thereof;

Ion exchange resins: including but not limited to amberlite IR120 and combinations and derivatives thereof;

and combinations of the noted excipients.

In the pharmaceutical formulation of the invention, in one embodiment the suspending agent is microcrystalline cellulose and carboxy methylcellulose sodium, the preservative is EDTA and potassium sorbate, the wetting agent is polyoxyethylene (20) sorbitan monooleate and the isotonicity adjusting agent is dextrose and/or glucose. In another embodiment the suspending agent is microcrystalline cellulose and carboxy methylcellulose sodium, the preservative is EDTA and benzalkonium chloride, the wetting agent is polyoxyethylene (20) sorbitan monooleate and the isotonicity adjusting agent is dextrose.

Preferable means for applying the formulation of the present invention to the nasal passages is by use of a pre-compression pump, such as a VP3, VP7 or modifications, model manufactured by Valois SA. Advantages of pumps of this type are beneficial as they will ensure that the formulation is not released or atomised until a sufficient force has been applied, otherwise smaller doses may be applied. Typically, these pre-compression pumps may be used with a bottle (glass or plastic) capable of holding 8-50 ml of a formulation. Each spray will typically deliver 50-100 µl of such a formulation, therefore, the device is capable of providing at least 100 metered doses. Suitably the formulation will be dispensed from a vessel fitted with a suitable pre-compression pump and nasal actuator, adapted to dispense 50 or 100 µl per actuation, preferably 50 µl. There is therefore provided a device adapted for intranasal delivery of a pharmaceutical formulation comprising a pharmaceutical formulation of the present invention.

A suitable dosing regime for the formulation of the present invention when administered to the nose would be for the patient to inhale slowly through the nose subsequent to the nasal cavity being cleared. During inhalation the formulation would be applied to one nostril while the other is manually compressed. This procedure would then be repeated for the other nostril.

Typically, one or two inhalations per nostril would be administered by the above procedure up to three times each day, possibly twice daily, ideally once daily. In one embodiment the formulation of the present invention is administered to the nose by means of one or two inhalations in each nostril, once per day.

It will be appreciated that the above dosing regime should be adjusted according to the patient's age, body weight and/or symptom severity.

The formulations of the present invention have potentially beneficial anti-inflammatory or anti-allergic effects, particularly upon topical administration to the nose. Hence, formulations according to the invention are useful in the treatment of inflammatory and/or allergic disorders of the nose, especially in once-per-day therapy.

Formulations according to the invention may be prepared by combining the ingredients in water. If necessary the pH may be adjusted as a final step. Formulations so prepared may then be filled into the receptacle.

Aqueous formulations of the invention may also be employed for rectal, aural, otic, oral, topical or parenteral administration or administration by inhalation for the treatment of other local inflammatory conditions (for example dermatitis, asthma, chronic obstructive pulmonary disease (COPD) and the like). For example formulations of the invention may be administered to the lung by nebulisation. Such formulations may employ excipients (for example preservatives, buffers and the like) appropriate for the route of administration.

Examples of disease states in which the formulation of the present invention has utility include inflammatory and/or allergic conditions of the nasal passages such as rhinitis for example seasonal and perennial rhinitis. It will be appreciated by those skilled in the art that reference herein to treatment extends to prophylaxis as well as the treatment of established conditions.

As mentioned above, formulations of the present invention are useful in medicine, in particular as an anti-inflammatory and anti-allergic agent.

There is thus provided as a further aspect of the invention a pharmaceutical formulation comprising levocabastine or a salt thereof and fluticasone furoate for use in medicine, particularly in the treatment of patients with an inflammatory and/or allergic condition. In one embodiment treatment is once-per-day.

In a further aspect of the invention, there is provided a pharmaceutical formulation comprising levocabastine or a salt thereof and fluticasone furoate for use in the treatment of patients with allergic rhinitis, for example seasonal allergic rhinitis, or perennial allergic rhinitis. In one embodiment treatment is once-per-day.

According to another aspect of the invention, there is provided the use of a formulation comprising levocabastine or a salt thereof and fluticasone furoate for the manufacture of a medicament for the treatment of patients with an inflammatory and/or allergic condition. In one embodiment treatment is once-per-day.

According to another aspect of the invention, there is provided the use of a formulation comprising levocabastine or a salt thereof and fluticasone furoate for the manufacture of a medicament for the treatment of patients with allergic rhinitis, for example seasonal allergic rhinitis, or perennial allergic rhinitis. In one embodiment treatment is once-per-day.

In a further or alternative aspect, there is provided a method for the treatment of a human or animal subject with an inflammatory and/or allergic condition, which method comprises administering to said human or animal subject an effective amount of a formulation comprising levocabastine or a salt thereof and fluticasone furoate. In one embodiment administration is once-per-day.

In an alternative aspect there is provided a method of treatment of allergic rhinitis, for example seasonal allergic rhinitis or perennial allergic rhinitis which comprises administering to a patient a pharmaceutically acceptable amount of a pharmaceutical formulation comprising levocabastine or a salt thereof and fluticasone furoate. In one embodiment administration is once-per-day.

The formulations of the present invention may be long-acting, therefore the formulation may be administered once daily and the dose may be selected so that the compounds have a therapeutic effect in the treatment of respiratory disorders (for example rhinitis) over 24 hours or more.

Levocabastine and salts thereof, in particular the hydrochloride and fluticasone furoate are known, commercially available compounds. Processes for preparing these compounds are well known in the art, for example from EP034415 and WO 02/12265.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

BRIEF DESCRIPTION OF THE SEVERAL VIEW(S) OF THE DRAWINGS

FIG. 1 depicts a study design for Study 1.
FIG. 2 depicts a study design for Study 2.
FIG. 3 depicts a study design for Study 3.
FIG. 4 depicts the XRPD of levocabastine crystalline anhydrate Form 1.
FIG. 5 depicts the XRPD of levocabastine crystalline anhydrate Form 2.
FIG. 6 depicts the XRPD of levocabastine crystalline anhydrate Form 3.
FIG. 7 depicts the $^{13}$C solid state NMR (SSNMR) spectrum of levocabastine in crystalline anhydrate Form 1.
FIG. 8 depicts the isotropic region of the $^{19}$F solid state NMR (SSNMR) spectrum of levocabastine in crystalline anhydrate Form 1.
FIG. 9 depicts the $^{13}$C solid state NMR (SSNMR) spectrum of levocabastine in crystalline anhydrate Form 2.
FIG. 10 depicts the isotropic region of the $^{19}$F solid state NMR (SSNMR) spectrum of levocabastine in crystalline anhydrate Form 2.
FIG. 11 depicts the $^{13}$C solid state NMR (SSNMR) spectrum of levocabastine in crystalline anhydrate Form 3.
FIG. 12 depicts the isotropic region of the $^{19}$F solid state NMR (SSNMR) spectrum of levocabastine in crystalline anhydrate Form 3 according to the present invention.
FIG. 13 depicts the $^{19}$F solid state NMR (SSNMR) spectrum of the formulation according to the present invention comprising levocabastine and fluticasone furoate.
FIG. 14 depicts, in a flow diagram, a process by which the formulation described in Example 1 may be prepared.

DETAILED DESCRIPTION OF THE INVENTION

The following non-limiting Examples illustrate the invention:

EXAMPLES

Example 1: Nasal Formulation Containing Fluticasone Furoate and Levocabastine Hydrochloride A formulation for intranasal delivery may be prepared with ingredients as follows:

| Ingredients | Quantity (% w/w) | Quantity (g per 50 L/spray) |
|---|---|---|
| Fluticasone furoate | 0.055 | 27.5 |
| Levocabastine Hydrocloride | 0.1 | 50 |
| Dextrose Anhydrous | 5.5 | 2750 |
| Dispersible cellulose | 1.65 | 825 |
| Polysorbate 80 | 0.0275 | 13.75 |
| Benzalkonium Chloride Solution | 0.0165 | 8.25 |
| Disodium Edetate | 0.0165 | 8.25 |
| Purified Water | to 100 | Qs |

Hydrochloric acid or sodium hydroxide may be added to adjust the pH to 6-8, if required.

Example 2: Method of Preparing the Formulation of Example 1

The formulation may be prepared by following the process of the flow diagram depicted in FIG. 14.

It has been observed that the levocabastine HCl salt converts during the preparation of formulations of the invention (e.g. as described in Examples 1 and 2) to levocabastine free base.

Levocabastine free base Forms 1 and 2 were observed during the form screen of the HCl salt and during pH solubility studies. Competitive ripening experiments conducted suggest that levocabastine Form 1 is the most stable form of the free base. Surprisingly, the Form of the free base in the final formulation was confirmed by $^{19}$F ssNMR to be Form 3.

The following provides information on the observed forms of levocabastine free base.

Preparation of Polymorphic Forms of Levocabastine Free Base

Levocabastine Free Base Form 1

A slurry of Levocabastine HCl (1.0 g) was added to a reactor and mixed with 100 ml of 4 mM sodium phosphate buffer (pH 7.5). The slurry was titrated with 1.0N NaOH to bring the pH to ~7. The slurry was then heated to 60° C. and stirred overnight. Solids were isolated by vacuum filtration.

Levocabastine Free Base Form 2

A slurry of Levocabastine HCl (1.0 g) was added to a reactor and mixed with 100 ml of 4 mM sodium phosphate buffer (pH 7.5). The slurry was titrated with 1.0N NaOH to bring the pH to ~7. Solids were isolated at 20° C. by vacuum filtration.

Levocabastine Free Base Form 3

Form 3 was prepared in two ways.

Preparation 1: Unseeded Levocabastine HCl (100 mg) was dissolved in 5 ml of Methanol at ~40° C. 2.2 ml of 0.1M NaOH was added to the solution at ~30° C. Crystallization was observed after the addition of ~1 ml of NaOH solution. The resulting solution was added slowly until crystallization was complete. The material was filtered and placed in a vial for characterization.

Preparation 2: Seeded Levocabastine HCl (2.5 g, 5.47 mmol) and Methanol (125 ml) were added to a reactor and heated to 60° C. to dissolve all solids. Seed of Preparation 1 was added to the mixture and solids were observed. Added remaining 0.1N NaOH by addition funnel over 30 min at 60° C. Cooled to 20° C. over 4 hrs and held overnight. The solids were isolated by vacuum filtration and dried on the funnel for 2 hrs. The batch was further dried by vacuum filtration at 40° C. under vacuum for 4 hrs. The material was isolated as dry solids (2.1 g).

X-Ray Powder Diffraction (XRPD)

The X-ray powder diffraction (XRPD) data of levocabastine polymorphic forms were acquired on a PANalytical X'Pert Pro powder diffractometer, modelPW3040 Pro, using an X'Celerator detector. The acquisition conditions were: radiation: Cu Kα, generator tension: 45 kV, generator current: 40 mA; step size: 0.017° 2θ; time per step: 500 seconds; incident beam optics: mirror optics—Cu W/Si (Focusing MPD), ½ degree fixed divergence slit, 0.02 radian soller slits; diffracted beam optics: programmable anti-scatter slit assembly (Xcelerator module) set to fixed ¼ degree anti-scatter slit, 0.02 radian soller slits., measurement temperature: 20-25° C. The sample was prepared by packing sample in a 1.0 mm capillary. Peak positions were obtained using PANalytical X'Pert Highscore Plus software. The margin of error is approximately ±0.1° 2θ for each of the peak assignments.

Solid State NMR (SSNMR)

$^{13}$C and $^{19}$F solid state NMR data of FIGS. 7-13 were acquired using a Bruker Avance 500 triple-resonance spectrometer operating at a $^1$H frequency of 499.98 MHz. The $^{13}$C SSNMR spectra shown were obtained using a cross-polarization pulse sequence with a Bruker 4-mm triple resonance magic-angle spinning probe at a rotor frequency of 8 kHz. A linear power ramp from 75 to 90 kHz was used on the $^1$H channel to enhance cross-polarization efficiency. Spinning sidebands were eliminated by a five-pulse total sideband suppression pulse sequence. $^1$H decoupling was obtained using the Spinal-64 sequence. The $^{19}$F SSNMR spectra shown were obtained using a cross-polarization pulse sequence with a Bruker 4-mm triple resonance magic-angle probe at a rotor frequency of 12.5 or 13.0 kHz. Characteristic $^{13}$C and $^{19}$F NMR peak positions are reported relative to tetramethylsilane at 0 ppm (parts per million) and are quoted to a precision of +/−0.2 ppm, because of instrumental variability and calibration.

Figure 7:
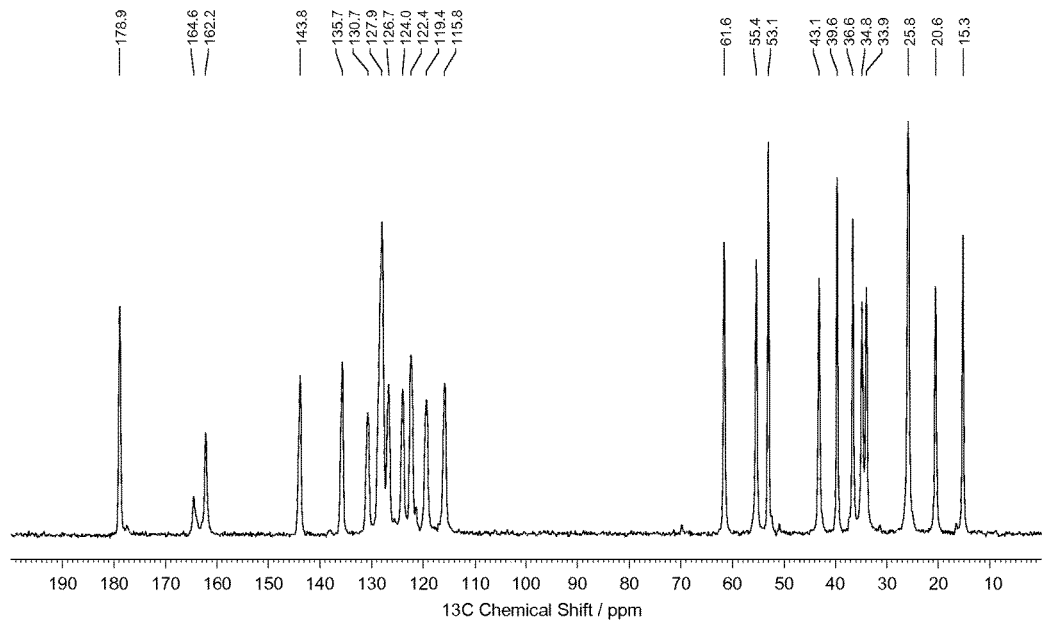

FIG. 7 depicts the $^{13}$C solid state NMR (SSNMR) spectrum of levocabastine in crystalline anhydrate Form 1. The solid state NMR spectrum was obtained on a spectrometer operating at a frequency of 125.73 MHz for $^{13}$C observation and a spinning speed of 8 kHz, according to the procedure described herein. The low intensity peaks are the result of a small amount of Form 3 present in the tested batch.

In an embodiment, the formulation of the present invention provides levocabastine in crystalline anhydrate Form 1 characterized by substantially the same $^{13}$C solid state nuclear magnetic resonance (SSNMR) as FIG. 7, wherein the SSNMR spectrum was obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

In a further embodiment, the formulation of the present invention provides levocabastine in crystalline anhydrate Form 1 characterized by a $^{13}$C SSNMR spectrum comprising chemical shifts at 178.9±0.2, 164.6±0.2, 162.2±0.2, 143.8±0.2, 135.7±0.2, 130.7±0.2, 127.9±0.2, 126.7±0.2, 124.0±0.2, 122.4±0.2, 119.4±0.2, 115.8±0.2, 61.6±0.2, 55.4±0.2, 53.1±0.2, 43.1±0.2, 39.6±0.2, 36.6±0.2, 34.8±0.2, 33.9±0.2, 25.8±0.2, 20.6±0.2, and 15.3±0.2 ppm.

Figure 8:
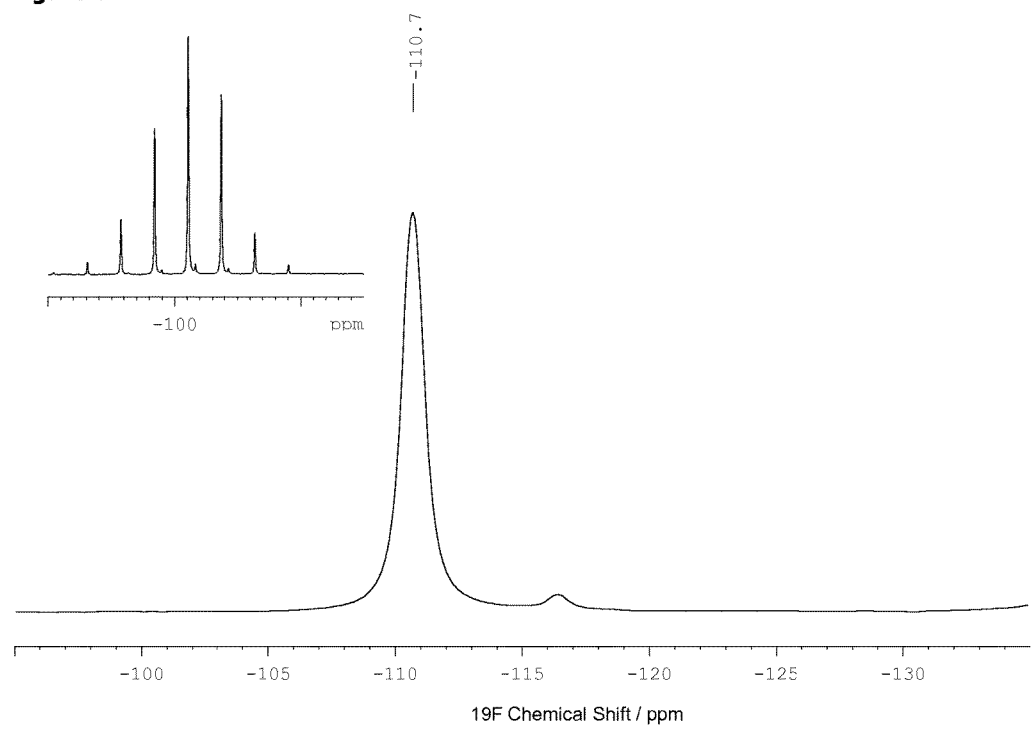

FIG. 8 depicts the isotropic region of the $^{19}$F solid state NMR (SSNMR) spectrum of levocabastine in crystalline anhydrate Form 1. The entire magic angle spinning spectrum is also provided (inset). The solid state NMR spectrum was obtained on a spectrometer operating at a frequency of 470.40 MHz for $^{19}$F observation and a spinning speed of 12.5 kHz, according to the procedure described herein. The $^{19}$F resonance at −116.5 ppm is a small amount of Form 3 present in the tested batch.

In an embodiment, the formulation of the present invention provides levocabastin in crystalline anhydrate Form 1 characterized by substantially the same $^{19}$F solid state nuclear magnetic resonance (SSNMR) spectrum as FIG. 8, wherein the SSNMR spectrum was obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

In a further embodiment, the formulation of the present invention provides levocabastine in crystalline anhydrate Form 1 characterized by a $^{19}$F SSNMR spectrum comprising of isotropic chemical shifts at −110.7±0.2 ppm.

Figure 9:
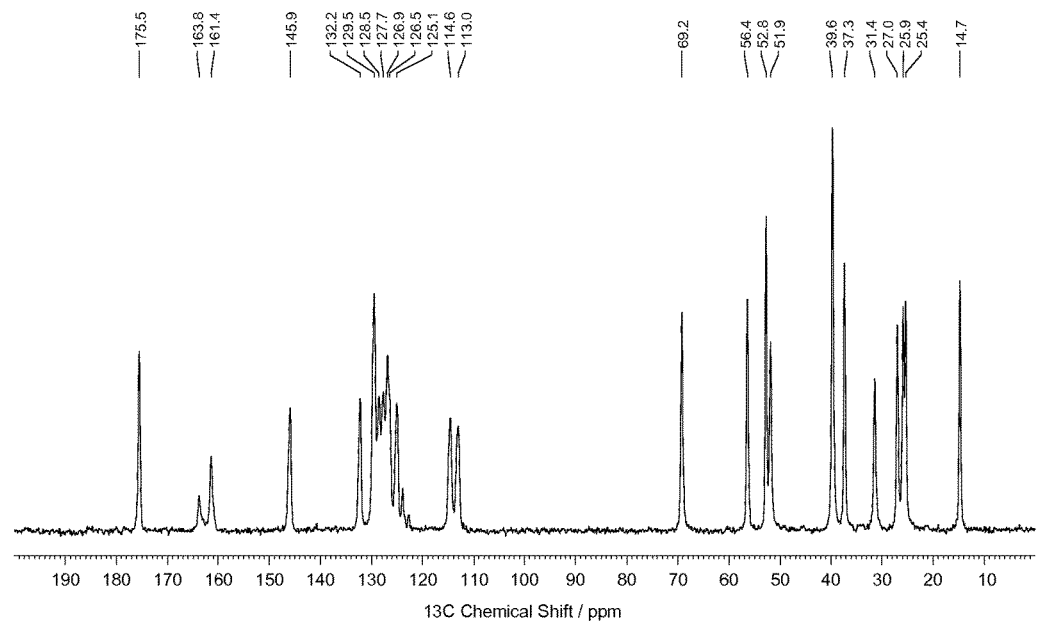

FIG. 9 depicts the $^{13}$C solid state NMR (SSNMR) spectrum of levocabastine in crystalline anhydrate Form 2. The solid state NMR spectrum was obtained on a spectrometer operating at a frequency of 125.73 MHz for $^{13}$C observation and a spinning speed of 8 kHz, according to the procedure described herein.

In an embodiment, the formulation of the present invention provides levocabastine in crystalline anhydrate Form 2 characterized by substantially the same $^{13}$C solid state nuclear magnetic resonance (SSNMR) spectrum as FIG. 9, wherein the SSNMR spectrum was obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

In a further embodiment, the formulation of the present invention provides levocabastine in crystalline anhydrate Form 2 characterized by a $^{13}$C SSNMR spectrum comprising chemical shifts at 175.5±0.2, 163.8±0.2, 161.4±0.2, 145.9±0.2, 132.2±0.2, 129.5±0.2, 128.5±0.2, 127.7±0.2, 126.9±0.2, 125.1±0.2, 114.6±0.2, 113.0±0.2, 69.2±0.2, 56.4±0.2, 52.8±0.2, 51.9±0.2, 39.6±0.2, 37.3±0.2, 31.4±0.2, 27.0±0.2, 25.9±0.2, 25.4±0.2, and 14.7±0.2 ppm.

Figure 10:
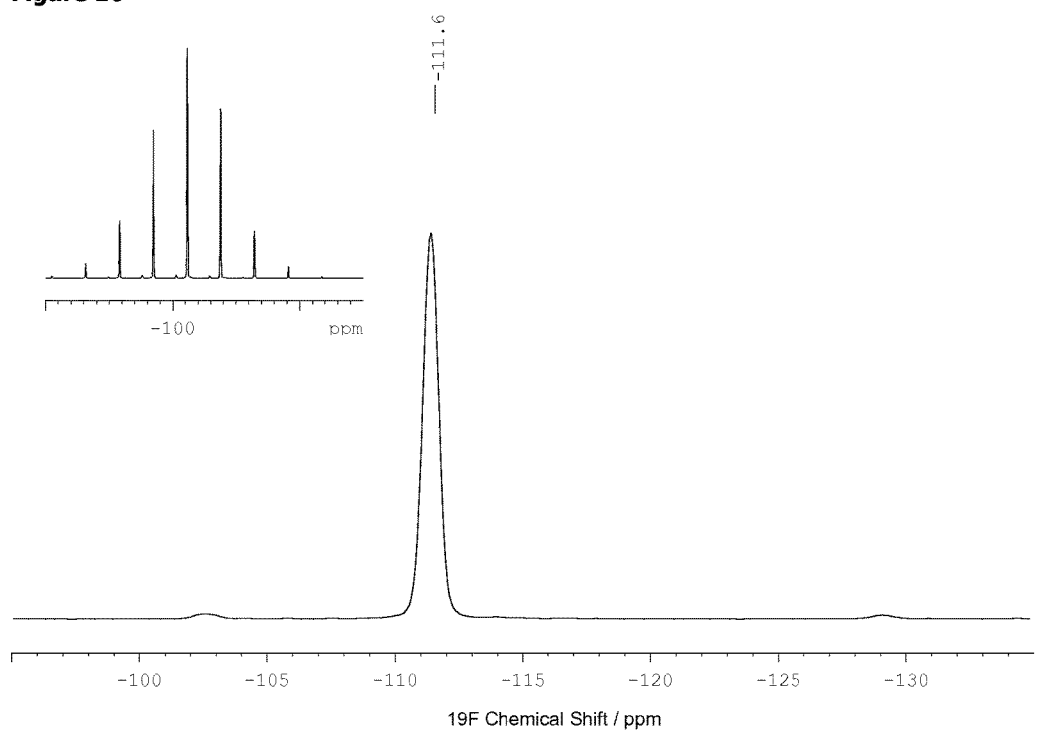

FIG. 10 depicts the isotropic region of the $^{19}$F solid state NMR (SSNMR) spectrum of levocabastine in crystalline anhydrate Form 2. The entire magic angle spinning spectrum is also provided (inset). The solid state NMR spectrum was obtained on a spectrometer operating at a frequency of 470.40 MHz for $^{19}$F observation and a spinning speed of 12.5 kHz, according to the procedures described herein.

In an embodiment, the formulation of the present invention provides levocabastine in crystalline anhydrate Form 2 characterized by substantially the same $^{19}$F solid state nuclear magnetic resonance (SSNMR) spectrum as FIG. 10, wherein the SSNMR spectrum was obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

In a further embodiment, the formulation of the present invention provides levocabastine in crystalline anhydrate Form 2 characterized by a $^{19}$F SSNMR spectrum comprising isotropic chemical shifts at −111.6±0.2 ppm.

Figure 11:
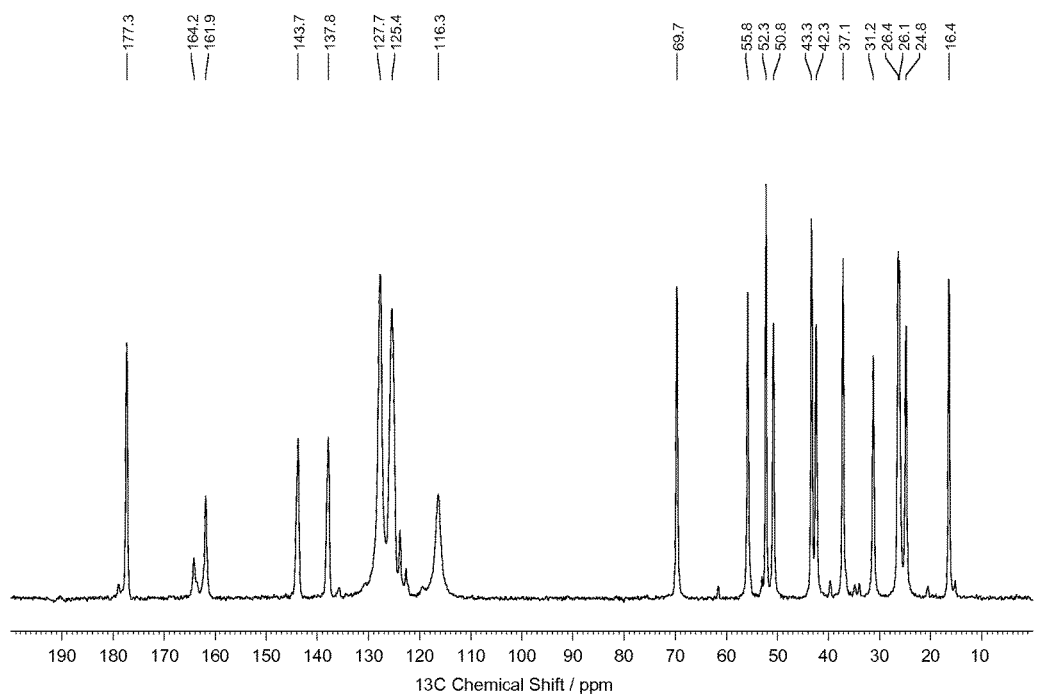

FIG. 11 depicts the $^{13}$C solid state NMR (SSNMR) spectrum of levocabastine in crystalline anhydrate Form 3. The solid state NMR spectrum was obtained on a spectrometer operating at a frequency of 125.73 MHz for $^{13}$C observation and a spinning speed of 8 kHz, according to the procedure described herein. The low intensity peaks are the result of a small amount of Form 1 present in the tested batch.

In an embodiment, the formulation of the present invention provides levocabastine in crystalline anhydrate Form 3 characterized by substantially the same $^{13}$C solid state nuclear magnetic resonance (SSNMR) spectrum as FIG. 11, wherein the SSNMR spectrum was obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

In a further embodiment, the formulation of the present invention provides levocabstine in crystalline anhydrate Form 3 characterized by a $^{13}$C SSNMR spectrum comprising chemical shifts at 177.3±0.2, 164.2±0.2, 161.9±0.2, 143.7±0.2, 137.8±0.2, 127.7±0.2, 125.4±0.2, 116.3±0.2, 69.7±0.2, 55.8±0.2, 52.3±0.2, 50.8±0.2, 43.3±0.2, 42.3±0.2, 37.1±0.2, 31.2±0.2, 26.4±0.2, 26.1±0.2, 24.8±0.2, and 16.4±0.2 ppm.

Figure 12:
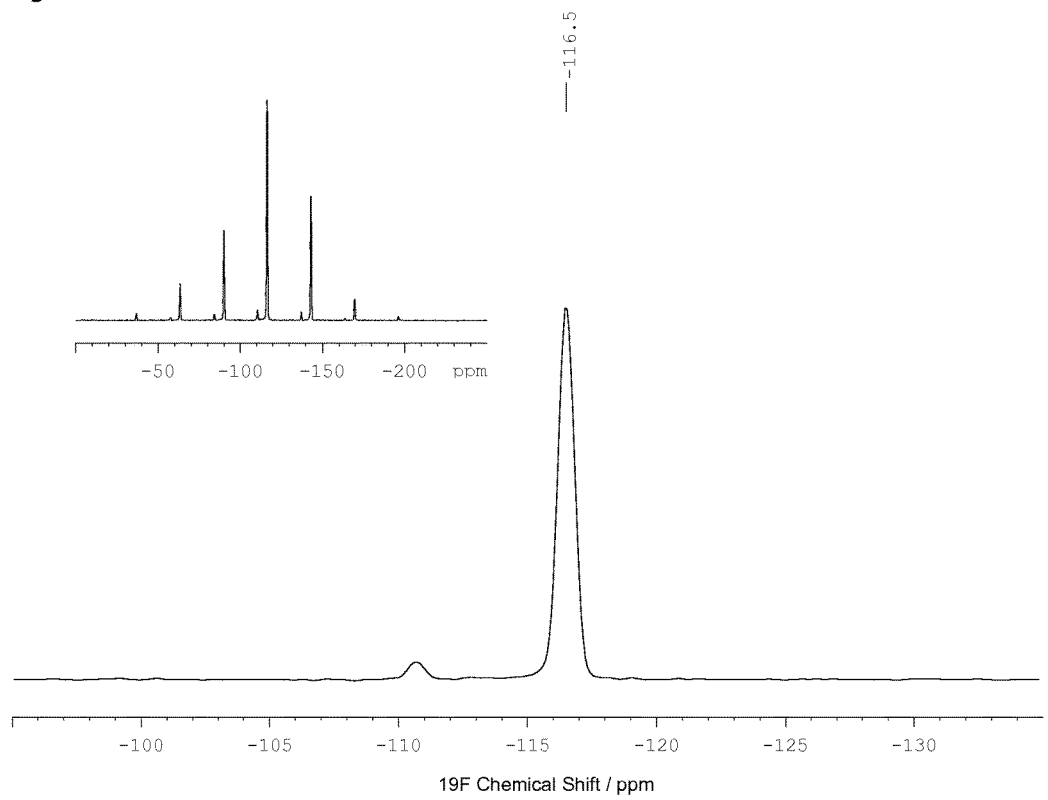

FIG. 12 depicts the isotropic region of the $^{19}$F solid state NMR (SSNMR) spectrum of levocabastine in crystalline anhydrate Form 3 according to the present invention. The solid state NMR spectrum was obtained on a spectrometer operating at a frequency of 470.40 MHz for $^{19}$F observation and a spinning speed of 12.5 kHz, according to the procedure described herein. The $^{19}$F resonance at −110.7 ppm is a small amount of Form 1 present in the tested batch.

In an embodiment, the formulation of the present invention provides levocabastine in crystalline anhydrate Form 3 characterized by substantially the same $^{19}$F solid state nuclear magnetic resonance (SSNMR) spectrum as FIG. 12, wherein the SSNMR spectrum was obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

In a further embodiment, the formulation of the present invention provides levocabstine in crystalline anhydrate Form 3 characterized by a $^{19}$F SSNMR spectrum comprising isotropic chemical shifts at −116.5±0.2 ppm.

Figure 13:
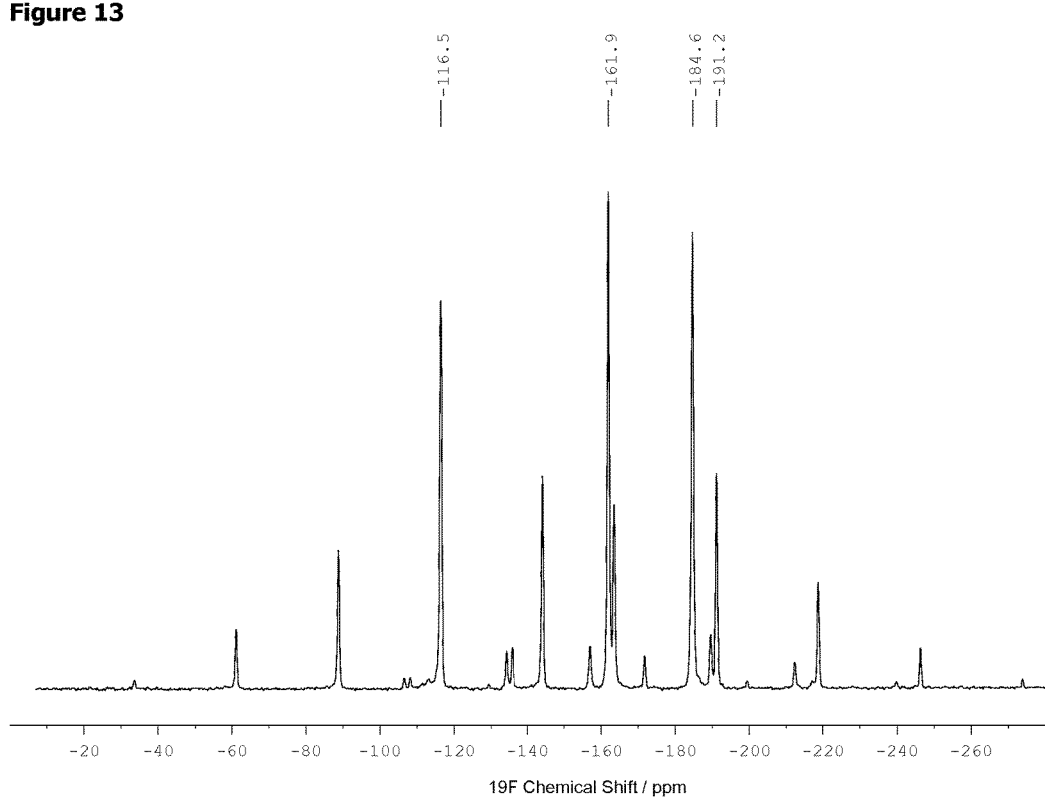
Figure 14:
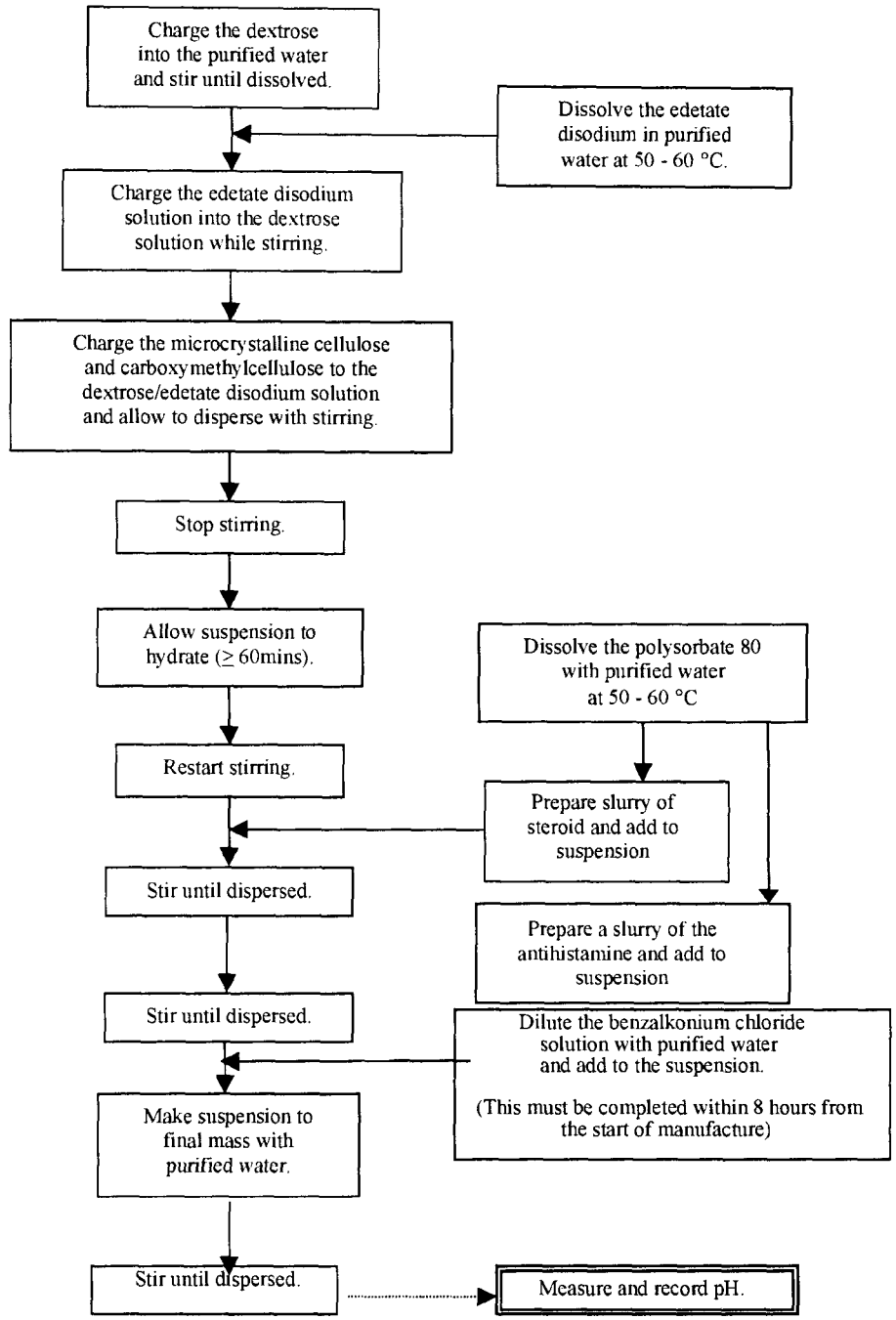

FIG. 13 depicts the $^{19}$F solid state NMR (SSNMR) spectrum of the formulation according to the present invention comprising levocabastine and fluticasone furoate. The solid state NMR spectrum was obtained on a spectrometer operating at a frequency of 470.40 MHz for $^{19}$F observation and a spinning speed of 13.0 kHz, according to the procedures described herein.

In an embodiment, the formulation of the present invention provides an $^{19}$F SSNMR spectrum comprising isotropic chemical shifts at −116.5±0.2 ppm and −161.9±0.2, −184.6±0.2, −191.2±0.2 ppm. These chemical shifts are consistent with those of levocabastine free base Form 3 and fluticasone furoate Form 1.

Clinical Studies

The effect of a combination comprising fluticasone furoate (FF) and levocabastine hydrochloride in human subjects is determined according to the studies described below.

Study 1

A randomised, double blind, placebo controlled, 4 part, 3 way, incomplete block crossover study to evaluate the effect of single and repeat doses of levocabastine, fluticasone furoate, placebo and a Fixed Dose Combination of fluticasone furoate/levocabastine administration in allergic rhinitis (AR) subjects Objectives and Endpoints Primary: Effect of 8 day treatment with intranasal FF/levocabastine on nasal symptoms elicited by an allergen chamber challenge in subjects with allergic rhinitis when administered once daily compared with FF and levocabastine alone.

Endpoint: TNSS and TOSS (Total Ocular Symtpom Score) on Day 8 after 8-day repeat FF/levocabastine compared to 8-day repeat FF alone, TNSS and TOSS on Day 8 after 8-day repeat FF/levocabastine compared to 8-day repeat levocabastine alone.

Secondary: To determine the time to onset of symptom relief following the first dose of FF/levocabastine relative to FF alone on nasal symptoms elicited by an allergen chamber challenge in subjects with allergic rhinitis.

Endpoint: The onset and magnitude of symptom relief on TNSS TOSS following a single dose of FF/levocabastine compared to FF alone.

The onset and magnitude of symptom relief on TNSS TOSS following a single dose of FF/levocabastine compared to levocabastine alone.

Study Design

Figure 1:
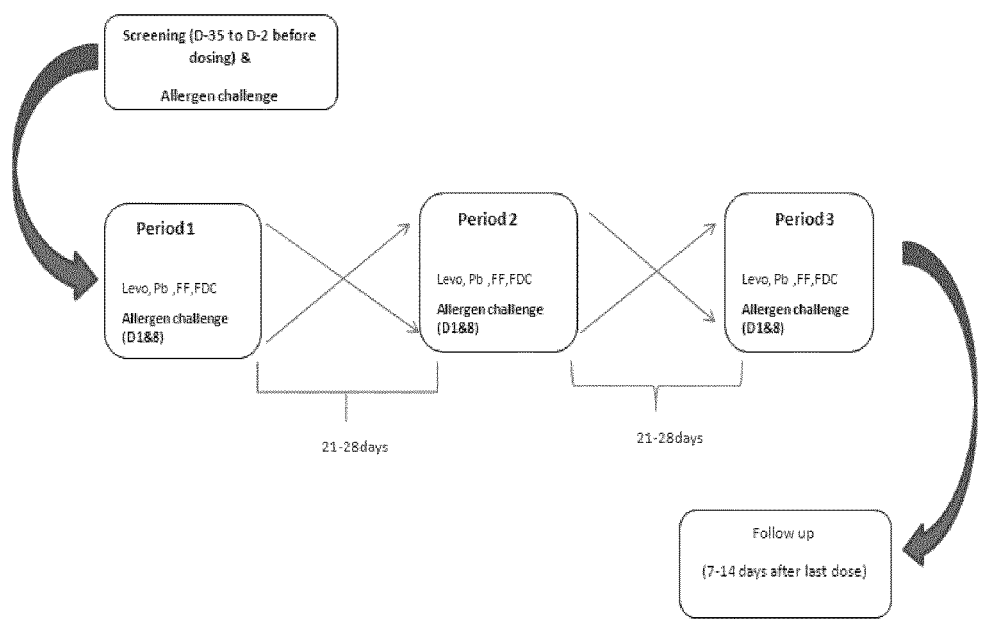

All subjects will complete the study as detailed in FIG. 1. The total expected study duration for each individual participating in the study will be a maximum of up to 20 weeks (including the screening and follow-up).

Approximately 72 subjects will be enrolled such that approximately 64 subjects complete dosing and critical assessments.

Study Treatment

Subjects will be assigned to a sequence of three treatments (e.g. ABC, BCD, ACD) in accordance with the randomisation schedule generated by Quantitative Sciences, prior to the start of the study, using validated internal software.

A description of each regimen is provided below:

A=Two, 50 µL sprays per nostril of FF Total dose 100 µg

B=Two, 50 µL sprays per nostril of levocabastine Total dose 200 µg

C=Two, 50 µL sprays per nostril of FF/levocabastine FDC. Total daily dose 110 µg FF and 200 µg levocabastine D=Two, 50 µL sprays per nostril of placebo.

Each subject will be assigned a randomization number before receiving their first dose of study medication. The randomization numbers will be assigned in sequential order starting with the lowest number first. Once a randomisation number has been assigned to a subject it cannot be reassigned to another subject.

The allergen challenge will be conducted in a sealed chamber as employed at the Vienna Challenge Chamber (VCC). The VCC has been used to evaluate established rhinitis therapies (including antihistamines and topical corticosteroids) and has the potential to discriminate not only

| | Study Treatment | | | |
|---|---|---|---|---|
| Product name: | Flucticasone furoate/ levocabastine | Flucticasone furoate | levocabastine | Placebo |
| Formulation description: | 0.05% w/w Fluticasone furoate and 0.10% w/w levocabastine in an aqueous suspension preserved with EDTA (0.015% w/w) and Benzalkonium Chloride (0.015% w/w). | 0.05% w/w Fluticasone furoate in an aqueous suspension preserved with EDTA (0.015% w/w) and Benzalkonium Chloride (0.015% w/w). | 0.10% w/w levocabastine in an aqueous suspension preserved with EDTA (0.015% w/w) and Benzalkonium Chloride (0.015% w/w). | An aqueous suspension preserved with EDTA (0.015% w/w) and Benzalkonium Chloride (0.015% w/w). |
| Dosage form: | Intranasal aqueous microsuspension | Intranasal aqueous microsuspension | Intranasal aqueous microsuspension | Intranasal aqueous microsuspension |
| Unit dose strength(s)/ Dosage level(s): | 25 µg/50 µg | 25 µg | 50 µg | N/A |
| Route/ Administration/ Duration: | intranasal | intranasal | intranasal | intranasal |
| Dosing instructions: | Two sprays in each nostril in the morning in a fasted state | Two sprays in each nostril in the morning in a fasted state | Two sprays in each nostril in the morning in a fasted state | Two sprays in each nostril in the morning in a fasted state |
| Physical description: | An amber glass bottle fitted with a white top actuated plastic metering atomising spray pump filled with a uniform white suspension | An amber glass bottle fitted with a white top actuated plastic metering atomising spray pump filled with a uniform white suspension | An amber glass bottle fitted with a white top actuated plastic metering atomising spray pump filled with a uniform white suspension | An amber glass bottle fitted with a white top actuated plastic metering atomising spray pump filled with a uniform white suspension |
| Device: | Amber glass screw top bottle with a white 50 mcl VP7 screw on pump with actuator, cap, and clip | Amber glass screw top bottle with a white 50 mcl VP7 screw on pump with actuator, cap, and clip | Amber glass screw top bottle with a white 50 mcl VP7 screw on pump with actuator, cap, and clip | Amber glass screw top bottle with a white 50 mcl VP7 screw on pump with actuator, cap, and clip |
| Method for individualizing dosage: | Metered atomising spray pump | Metered atomising spray pump | Metered atomising spray pump | Metered atomising spray pump | efficacy but also onset and duration of action, depending on the relationship of dosing to allergen exposure [Zieglmayer, 2008].

The challenge agents to be used in the chamber are supplied by Allergon in Sweden and are a mixture of 4 grass types (Timothy, Orchard grass, Perennial rye grass and sweet vernal grass).

Pharmacodynamic Analyses 72 subjects will be recruited. All the subjects with at least one period of data will be included in the analysis. No imputation will be done for missing data. Nasal symptoms (nasal congestion/blockage, itch, sneeze and rhinorrhoea) will be scored on a categorical scale from 0 to 3. For each subject and time point, the total nasal symptom score (TNSS) will be calculated as the sum of the response for nasal congestion, nasal itch, sneeze and rhinorrhoea. Mean profile TNSS (and its individual components) plots over time (including all pre-dose time points) will be produced by treatment groups.

The primary analysis will be the comparison between FDC and FF alone and the comparison between FDC and levocabastine alone of weighted mean TNSS (0-3) hours post start of challenge chamber on Day 8 (i.e. 1-4 hours post dose). These two analyses will be done separately in the same way as detailed below.

The derived parameter will be analysed using a mixed effects analysis of variance model adjusting for terms due to baseline (pre-challenge on day 8), period, treatment, and treatment by baseline interaction term fitted as fixed effects, with subject fitted as random effect. An estimate of the treatment comparisons (FDC vs. FF or FDC vs. levocabastine) will be calculated between the adjusted means (LS-means) along with the associated 95% confidence interval. Individual components of TNSS score will be analysed in a similar manner. A term for carry-over may be fitted if necessary. Secondary analyses will be made on the following comparisons: FF vs. levocabastine, levocabastine vs. Placebo, FF vs. Placebo and FDC vs. Placebo.

Study 2

A randomized, double-blind, placebo controlled, 3 way cross over study in subjects with allergic rhinitis to assess the effect of intranasal repeat doses of Levocabastine when administered once daily or twice daily on the symptoms of rhinitis in an allergen challenge chamber.

Objectives and Endpoints

Primary

To investigate the non-inferiority of effect of 7 days treatment with levocabastine on nasal symptoms elicited by an allergen chamber challenge (Environmental Exposure Chamber) in subjects with allergic rhinitis when administered once daily compared with twice daily.

Endpoint: TNSS after 7 days of treatment when administered once daily compared to twice daily measured at trough PK levels (i.e. approximately 24 hours and 12 hours respectively) after the last active dose on Day 7.

To investigate the superiority of effect of 7 days treatment with levocabastine (once and twice daily) on nasal symptoms elicited by an allergen chamber challenge (Environmental Exposure Chamber) in subjects with allergic rhinitis compared to placebo.

Endpoint: Total Nasal Symptom Score (TNSS) after 7 days of Levocabastine compared to placebo measured at trough PK levels after the last dose on Day 7.

Secondary

To investigate the tolerability of Steady State intranasal doses of Levocabastine alone in healthy male and female subjects.

Endpoint: Individual components (nasal congestion, rhinorrhoea, nasal itch and sneeze);

Tolerability of once and twice daily intranasal levocabastine.

Study Design

Figure 2:
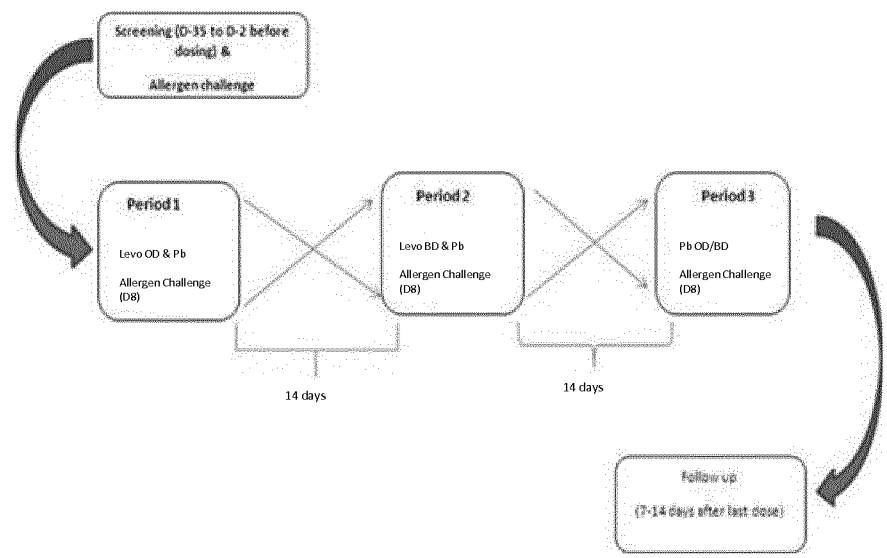

The study design is shown in FIG. 2.

All individuals will undergo an initial screening visit to assess their eligibility to participate in the study. All subjects will receive treatments in all three periods and the sequence will be determined by using a randomisation code in accordance with the randomisation schedule.

All subjects will receive treatments in all three periods and the sequence will be determined by using a randomisation code. Subjects will be randomly assigned to one of six treatment sequences (ABC, BCA, CAB, ACB, BAC, CBA) in accordance with the randomisation schedule.

Subjects will be required to administer drug at 12 hourly intervals (twice daily) in all three treatment regimens. Subjects will be given two bottles: a "morning" bottle and an "evening" bottle (labelled appropriately). When randomised to OD the "morning" bottle will contain active and the "evening" will contain placebo. When randomised to BD both bottles will contain active. When randomised to placebo both bottles will contain placebo. In all three regimens first dose will start with the morning dose, if feasible. First and last dose will be administered in the clinic. All remaining dosing will be done at home. There will be a 14-20 day washout between each treatment period regimen. Subjects are required to remain overnight at the clinic on Day 7 of each period with an allergen challenge done at 12 hours post dose (Day 8, i.e. approximately 24 hours post dose for OD and 12 hours post active dose for BD). Refer to table below.

| Allergen Challenge Visit | Dosing[1] | Allergen Challenge Time-Point |
|---|---|---|
| Screening Visit | N/A | −35 to −2 Days prior to dosing |
| Period 1, Day 8 | Treatment A: Levo (2 puffs per nostril) a.m. and 2 puffs placebo p.m. Total Dose: 200 μg daily | Approximately 12 hours post dosing (ie 24 hours post active dosing) |
| Period 2, Day 8 | Treatment B: Levo (2 puffs per nostril) a.m. and 2 puffs Levo p.m. Total Dose: 400 μg daily | Approximately 12 hours post dosing |
| Period 3, Day 8 | Treatment C: Placebo (2 puffs per nostril) a.m. and 2 puffs placebo p.m. | Approximately 12 hours post dosing |

The order of treatments A, B & C will be randomised across periods 1, 2 & 3.

Administration of the doses will occur in the morning and evenings. Attempts should be made to dose as close as possible for each subject throughout the study and subjects should be instructed on the dosing times. Allergen challenges should be performed as consistently as possible for each subject in each period Day 8 by the site according to the above table and timings. The time and date of the last 2 doses will be entered into the subject's source notes. All subjects will return for a follow up visit 7-14 days after last dose after Period 3.

Follow Up:

Subjects will be required to attend the unit for a follow up visit 7-14 days after the last dose of study medication after Period 3. The total expected study duration for each participating individual will be a maximum of 13 weeks, including screening and follow up.

Study Treatment
Investigational Product and Other Study Treatment

| Product name: | Placebo | Levocabastine |
|---|---|---|
| Formulation description: | Aqueous suspension preserved with EDTA (0.015% w/w) and Benzalkonium Chloride (0.015% w/w). | Levocabastine 0.10% w/w Levocabastine in an aqueous suspension preserved with EDTA (0.015% w/w) and Benzalkonium Chloride (0.015% w/w). |
| Dosage form: | Intranasal aqueous microsuspension | Intranasal aqueous microsuspension |
| Unit dose strength(s)/Dosage level(s): | 0 μg | 50 μg |
| Route/Administration/Duration: | Intranasal | Intranasal |
| Dosing instructions: | "Morning": Two sprays in each nostril in the morning in a fasted state. "Evening": Two sprays in each nostril in the evening in a fasted state. | "Morning": Two sprays in each nostril in the morning in a fasted state. "Evening" Two sprays in each nostril in the evening in a fasted state. |
| Physical description: | An amber glass bottle fitted with a white top actuated plastic metering atomising spray pump filled with a uniform white suspension | An amber glass bottle fitted with a white top actuated plastic metering atomising spray pump filled with a uniform white suspension |
| Manufacturer/source of procurement: | GlaxoSmithKline | GlaxoSmithKline |

Challenge Agents

The pollen used for allergen challenge in the EEC will be short ragweed pollen (*Ambrosia artemisiifolia*, sourced from Greer Laboratories, Inc., Lenoir, Carolina). Airborne ragweed exposure is within 3500±500 pollen grains/m$^3$ in the EEC.

Pharmacodynamic Analyses

Nasal symptoms (nasal congestion/blockage, itch, sneeze and rhinorrhoea) will be scored on a categorical scale from 0 to 3. For each subject and time point, the total nasal symptom score (TNSS) will be calculated as the sum of the response for nasal congestion, nasal itch, sneeze and rhinorrhoea. Mean profile TNSS (and its individual components) plots over time (including all pre-dose time points) will be produced by treatment group.

The primary analysis will be the comparison between treatments on weighted mean TNSS (0-4) hours post start of challenge chamber on Day 8 (i.e. approximately 24 or 12 hours post active dose). The derived parameter will be analysed using a mixed effects analysis of variance model adjusting for terms due to baseline (pre-challenge on day 8), period, treatment and treatment by baseline interaction term fitted as fixed effects, with subject fitted as random effect. Estimates of the three pairwise treatment differences (Levo BD v placebo, Levo OD v placebo, and Levo OD v Levo BD B) will be calculated between the adjusted means (LSmeans) along with the associated 95% confidence intervals. This analysis will be performed on both ITT and PP populations.

Individual components of TNSS score will be analysed in a similar manner. A term for carry-over may be fitted if necessary. Mean profile plots showing the mean 95% confidence interval value by treatment of each endpoint at each time-point on Day 8 will also be produced. To obtain the estimates for the profile plots over 0-4 hrs in the allergen challenge chamber a mixed effects analysis of variance model will be used fitting period, time, treatment and time*treatment interaction as fixed effects, with subject as a random effect and time as a repeated effect. Baseline (pre-challenge TNSS on Day 8) and baseline*time interaction may be included in the model as covariate.

The individual symptom scores of TNSS (nasal congestion/blockage, rhinorrhoea itch, and sneeze) will also be analysed and presented as above.

Study 3

A relative bioavailability study to compare the pharmacokinetics of a fixed dose combination of fluticasone furoate and levocabastine with levocabastine and fluticasone furoate alone.

This study aims to determine the bioavailability of a fixed dose combination of fluticasone furoate and levocabastine with levocabastine and fluticasone furoate alone in healthy male and female volunteers. This will be an open-label, randomized, repeat dose, three-way crossover study. Subjects will receive treatment each morning for 7 consecutive days for each of three treatment periods, separated by a minimum 14 day washout period. Blood samples for pharmacokinetic analysis will be taken at regular intervals after dosing on Day 7 of each treatment period. A follow-up visit will take place 7-14 days post last dose. A minimum of 30 patients will be enrolled, including 12 patients of Korean heritage.

Figure 3:
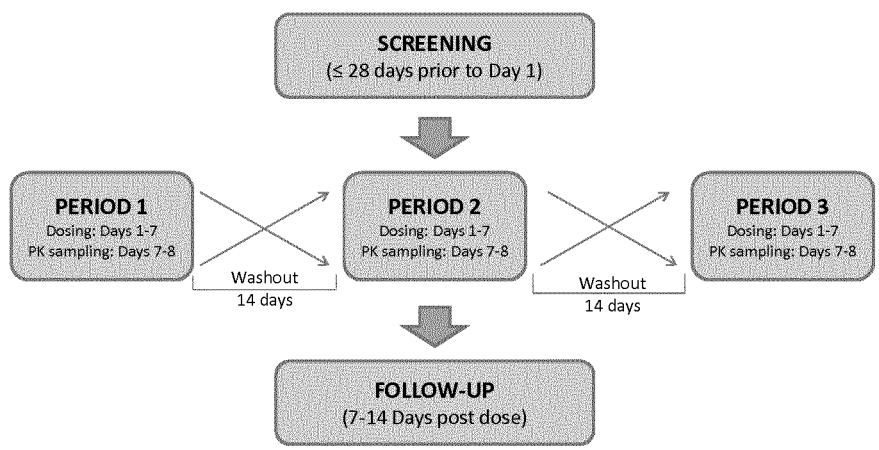
Figure 4:
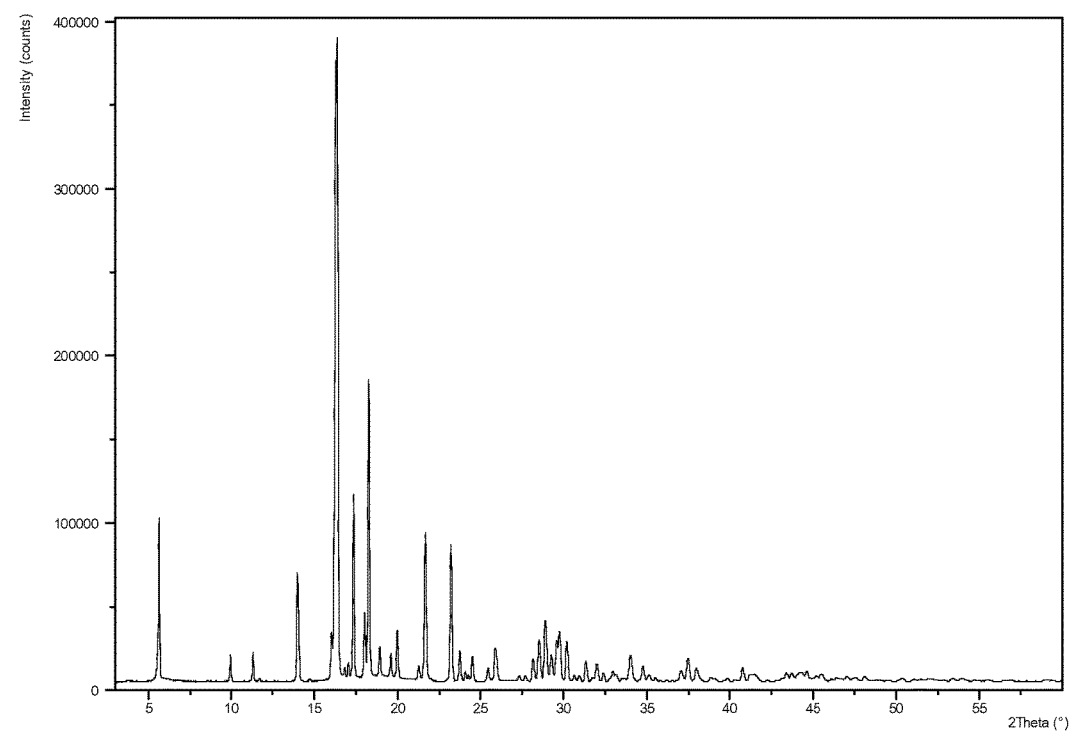
FIG. 4 depicts the XRPD of levocabastine crystalline anhydrate Form 1. In an embodiment, the formulation of the present invention provides levocabastine in polymorphic Form 1 which exhibits an X-ray powder diffraction (XRPD) pattern that has characteristic peaks, expressed in degrees 2θ, at about 5.6, 14.0, 16.3, 16.4, 17.4, 18.0, 18.3, 21.7, 23.2°±0.1.
Figure 5:
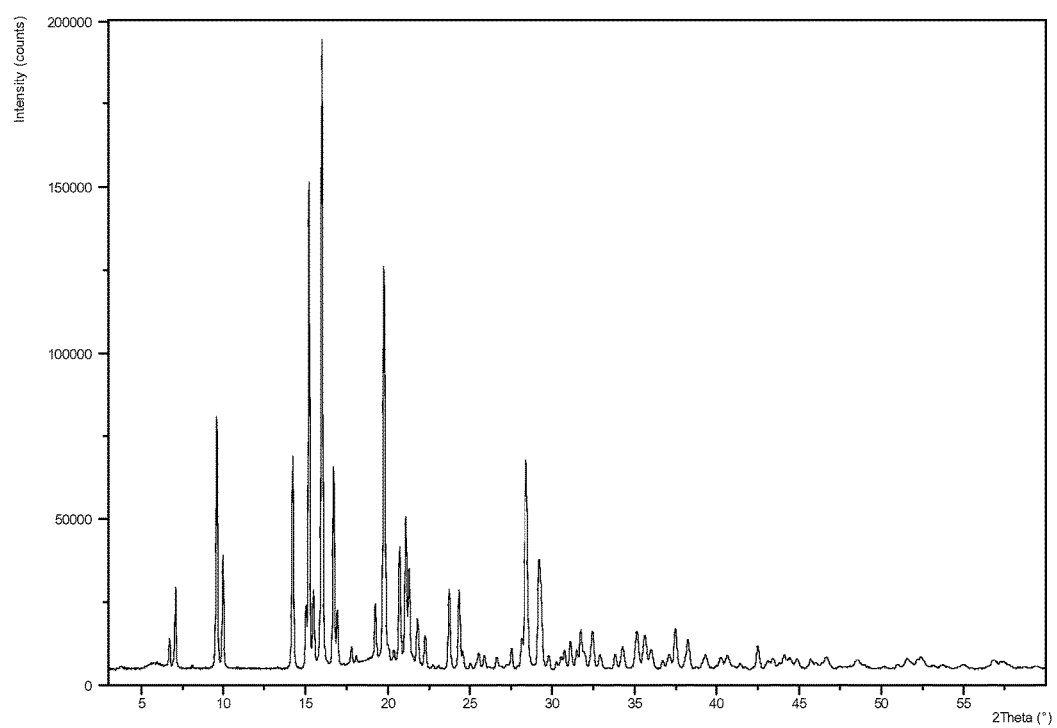
FIG. 5 depicts the XRPD of levocabastine crystalline anhydrate Form 2. In an embodiment, the formulation of the present invention provides levocabastine in polymorphic Form 2 which exhibits an X-ray powder diffraction (XRPD) pattern that has characteristic peaks, expressed in degrees 2θ, at about 6.7, 7.1, 9.6, 10.0, 14.2, 15.2, 16.0, 16.7, 19.8, 21.1, 28.4°±0.1.
Figure 6:
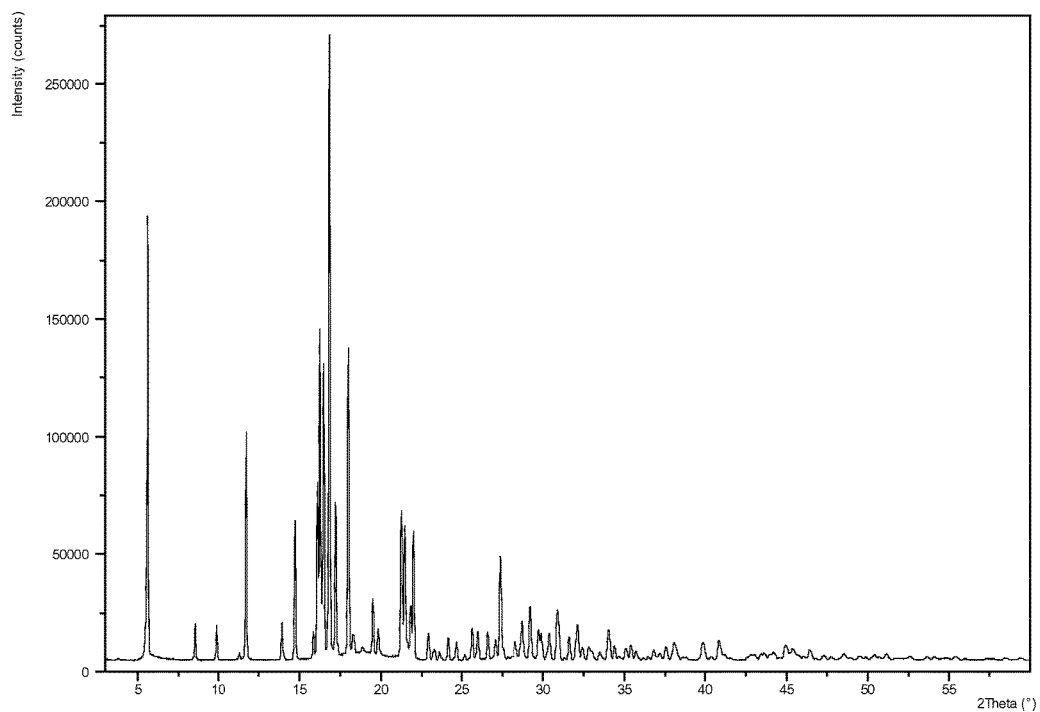
FIG. 6 depicts the XRPD of levocabastine crystalline anhydrate Form 3. In an embodiment, the formulation of the present invention provides levocabastine in polymorphic Form 3 which exhibits an X-ray powder diffraction pattern (XRPD) that has characteristic peaks, expressed in degrees 2θ, at about 5.6, 8.6, 9.9, 11.7, 14.7, 16.1, 16.3, 16.5, 16.8, 17.2, 18.0, 21.3, 21.5, 22.0, 27.3°±0.1

The study design is shown in FIG. 3.

| Objectives | Endpoints |
|---|---|
| Primary | |
| To determine the relative bioavailability of FF and LEV when administered as a FDC compared with each of the components administered alone in healthy male and female subjects | Plasma concentrations of FF and LEV. PK parameters (AUC, Cmax,) for both FF and LEV. |
| Secondary | |
| To investigate the pharmacokinetics of FF and LEV in healthy Korean male and female subjects | PK parameters (AUC, Cmax, tmax) for both FF and LEV alone and in combination |
| To investigate the pharmacokinetics of steady state intranasal doses of FF and LEV when administered as a FDC compared with each of the components administered alone in healthy male and female subjects | Tmax |

Treatment Assignment

Subjects will be assigned to one of six treatment sequences (ABC, ACB, BAC, BCA, CAB, CBA) in accordance with the randomization schedule generated by Clinical Statistics, prior to the start of the study, using validated internal software.

A description of each regimen is provided below:

A=Two, 50 μl sprays per nostril (4 sprays in total) of FF/LEV FDC. Total daily dose 110 ug FF and LEV 200 ug.

B=Two, 50 ul sprays per nostril (4 sprays in total) of FF. Total dose 110 ug.

C=Two, 50 ul sprays per nostril (4 sprays in total) of LEV. Total dose 200 ug

Each subject will be assigned a randomization number before receiving their first dose of study medication. The randomization numbers will be assigned in sequential order starting with the lowest number first. Once a randomization number has been assigned to a subject it cannot be reassigned to another subject.

Bioavailability

This study is designed to estimate the relative bioavailability of each of the components FF and LEV when administered as the FDC relative to FF and LEV when administered alone. No formal hypothesis will be tested. For each primary pharmacokinetic endpoint, point estimates and corresponding 90% confidence intervals will be constructed for the ratio of the geometric mean of the test treatment to the geometric mean of the reference treatment, $\mu(test)/\mu(reference)$.

Study Treatment

Investigational Product and Other Study Treatment

What is claimed is:

1. A pharmaceutical formulation comprising levocabastine

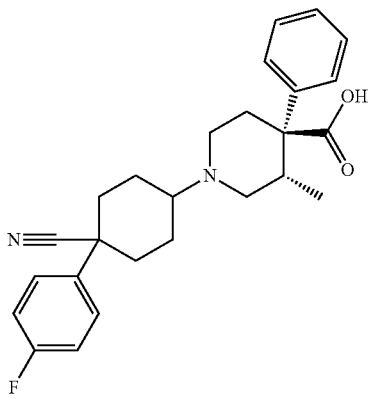 [SMILES: C[C@@H]1CN(C2CCC(C#N)(c3ccc(F)cc3)CC2)CC[C@]1(C(=O)O)c1ccccc1]

or a salt thereof and fluticasone furoate.

| | Study Treatment | | |
|---|---|---|---|
| Product name: | Flucticasone furoate/ Levocabastine (FDC) | Flucticasone furoate (Avamys commercial product) | Levocabastine (Livostin commercial product) |
| Formulation description: | 0.05% w/w Fluticasone furoate and 0.10% w/w Levocabastine in an aqueous suspension preserved with EDTA (0.015% w/w) and Benzalkonium Chloride (0.015% w/w). | 0.05% w/w Fluticasone furoate in an aqueous suspension preserved with EDTA (0.015% w/w) and Benzalkonium Chloride (0.015% w/w). | 0.05% w/w Levocabastine in an aqueous suspension preserved with EDTA and Benzalkonium Chloride. |
| Dosage form: | Intranasal aqueous microsuspension | Intranasal aqueous microsuspension | Intranasal aqueous microsuspension |
| Unit dose strength(s)/Dosage level(s): | 27.5 µg/50 µg | 27.5 µg | 50 µg |
| Route/ Administration/ Duration: | intranasal | Intranasal | Intranasal |
| Dosing instructions: | Two sprays per nostril in the morning in a fasted state | Two sprays per nostril in the morning in a fasted state | Two sprays per nostril in the morning in a fasted state |
| Physical description: | An amber glass bottle fitted with a white top actuated plastic metering atomising spray pump filled with a uniform white suspension | A side actuating white and blue plastic device surrounding an amber glass bottle fitted with a plastic metering atomising spray pump filled with a uniform white suspension | An white plastic bottle fitted with a white top actuated plastic metering atomising spray pump |
| Device: | Amber glass screw top bottle with a white 50 mcl VP7 screw on pump with actuator, cap, and clip | Mistpro commercial device. A side actuating white and blue plastic device surrounding an amber glass bottle fitted with a plastic 50 mcl metering atomising spray pump, with a blue cap | A white plastic bottle fitted with a white top actuated plastic 100 mcl metering atomising spray pump with a cap |
| Manufacturer/ source of procurement: | GlaxoSmithKline | GlaxoSmithKline | Johnson & Johnson, Pacific |
| Method for individualizing dosage: | Metered atomising spray pump | Metered atomising spray pump | Metered atomising spray pump |

2. A pharmaceutical formulation according to claim 1, comprising levocabastine hydrochloride and fluticasone furoate.

3. A pharmaceutical formulation according to claim 1, wherein fluticasone furoate and levocabastine or salt thereof are present in the form of suspended particles.

4. A pharmaceutical formulation according to claim 1, which is an aqueous pharmaceutical formulation.

5. A pharmaceutical formulation according to claim 1, which is suitable for intranasal delivery.

6. A pharmaceutical formulation according to claim 1, which further comprises one or more suspending agents.

7. A pharmaceutical formulation according to claim 1, which comprises one or more preservatives.

8. A pharmaceutical formulation according to claim 1, which comprises one or more wetting agents.

9. A pharmaceutical formulation according to claim 1, which comprises one or more isotonicity adjusting agents.

10. A pharmaceutical formulation according to claim 9, characterised in that it is isotonic with fluids of the nasal cavity.

11. A pharmaceutical formulation according to claim 1, which comprises a buffer.

12. A pharmaceutical formulation according to claim 4, which is pH adjusted to between 6 and 8.

13. A pharmaceutical formulation according to claim 1, which comprises one or more taste-masking agents.

14. A pharmaceutical formulation according to claim 1, wherein fluticasone furoate is present within the formulation in an amount of from 0.005% to 1% (w/w), based on the total weight of the formulation.

15. A pharmaceutical formulation according to claim 1, wherein levocabastine or a salt thereof is present within the formulation in an amount of from 0.0005% to 2% (w/w), based on the total weight of the formulation.

16. A pharmaceutical formulation according to claim 1, which comprises
   (i) an aqueous suspension of levocabastine or a salt thereof;
   (ii) an aqueous suspension of fluticasone furoate;
   (iii) one or more suspending agents;
   (iv) one or more preservatives;
   (v) one or more wetting agents;
   (vi) a buffer;
   (vii) one or more isotonicity adjusting agents; and optionally
   (viii) one or more taste-masking agents.

17. A device adapted for intranasal delivery of a pharmaceutical formulation comprising a pharmaceutical formulation as claimed in claim 1.

18. A method of treatment of allergic rhinitis which comprises administering to a patient a pharmaceutically acceptable amount of a pharmaceutical formulation according to claim 1.

19. The method according to claim 18, wherein the administration is once-per-day.

20. A method for the treatment of a human subject with an inflammatory and/or allergic condition, which method comprises administering to said human subject an effective amount of a pharmaceutical formulation according to claim 1.

* * * * *